(12) United States Patent
Kim et al.

(10) Patent No.: US 10,479,978 B2
(45) Date of Patent: Nov. 19, 2019

(54) POSTNATAL ADHERENT CELLS AND PREPARATION METHOD THEREFOR

(71) Applicant: CHA BIOTECH CO., LTD., Seoul (KR)

(72) Inventors: Hye Sun Kim, Seongnam-si (KR); Ah Reum Kang, Seongnam-si (KR); Hyun Ju Kim, Seongnam-si (KR); Kung Mi Park, Seoul (KR); Sang Un Joo, Seoul (KR)

(73) Assignee: CHA BIOTECH CO., LTD., Seoul (KR)

( * ) Notice: Subject to any disclaimer, the term of this patent is extended or adjusted under 35 U.S.C. 154(b) by 0 days.

(21) Appl. No.: 15/577,633

(22) PCT Filed: May 27, 2016

(86) PCT No.: PCT/KR2016/005636
§ 371 (c)(1),
(2) Date: Nov. 28, 2017

(87) PCT Pub. No.: WO2016/190704
PCT Pub. Date: Dec. 1, 2016

(65) Prior Publication Data
US 2018/0112184 A1    Apr. 26, 2018

(30) Foreign Application Priority Data

May 28, 2015   (KR) .......................... 10-2015-0075374
May 27, 2016   (KR) .......................... 10-2016-0065593

(51) Int. Cl.
*C12N 5/0775*   (2010.01)
*C12N 5/073*    (2010.01)
*A61K 35/50*    (2015.01)
*A61L 27/36*    (2006.01)

(52) U.S. Cl.
CPC ............ *C12N 5/0665* (2013.01); *A61K 35/50* (2013.01); *A61L 27/3604* (2013.01); *A61L 27/3683* (2013.01); *A61L 27/3687* (2013.01); *A61L 27/3691* (2013.01); *C12N 5/0605* (2013.01); *C12N 2500/02* (2013.01); *C12N 2501/11* (2013.01); *C12N 2501/119* (2013.01); *C12N 2501/12* (2013.01); *C12N 2501/15* (2013.01); *C12N 2501/165* (2013.01); *C12N 2501/70* (2013.01); *C12N 2501/91* (2013.01)

(58) Field of Classification Search
None
See application file for complete search history.

(56) References Cited

U.S. PATENT DOCUMENTS

| 8,562,973 | B2 | 10/2013 | Edinger et al. |
| 2007/0243172 | A1 | 10/2007 | Ra et al. |
| 2010/0112697 | A1 | 5/2010 | Kim et al. |
| 2014/0219970 | A1 | 8/2014 | Edinger et al. |

FOREIGN PATENT DOCUMENTS

| KR | 10-2007-0101756 A | 10/2007 |
| KR | 10-2008-0104850 A | 12/2008 |
| WO | WO 2011/127113 A1 | 10/2011 |

OTHER PUBLICATIONS

International Search Report dated Aug. 19, 2016, in PCT/KR2016/005636 filed May 27, 2016.
H.M. Yun et al., "Placenta-derived mesenchymal stem cells improved memory dysfunction in an $A\beta_{1\text{-}42}$-infused mouse model of Alzheimer's disease" (2013), Cell Death and Disease, vol. 4, No. 12, e958; doi:10.1038/cddis.2013.490, published online Dec. 12, 2013, pp. 1-10.
Olga Genbacev et al., "Regulation of Human Placental Development by Oxygen Tension" (1997), Science, vol. 277, No. 5332, DOI: 10.1126/science.277.5332.1669. (1997), downloaded from www.sciencemag.org on Nov. 25, 2015, pp. 1669-1672 (5 pages).

*Primary Examiner* — Daniel C Gamett
(74) *Attorney, Agent, or Firm* — Oblon, McClelland, Maier & Neustadt, L.L.P.

(57) ABSTRACT

Enhanced postnatal adherent cells and a preparation method therefor are provided. The preparation method of enhanced postnatal adherent cells can increase the yield and the proliferation rate of adherent cells from placental tissues; and prepare adherent cells, which secrete proteins effective for neurological diseases and have an improved ability for movement to damaged tissues.

11 Claims, 12 Drawing Sheets

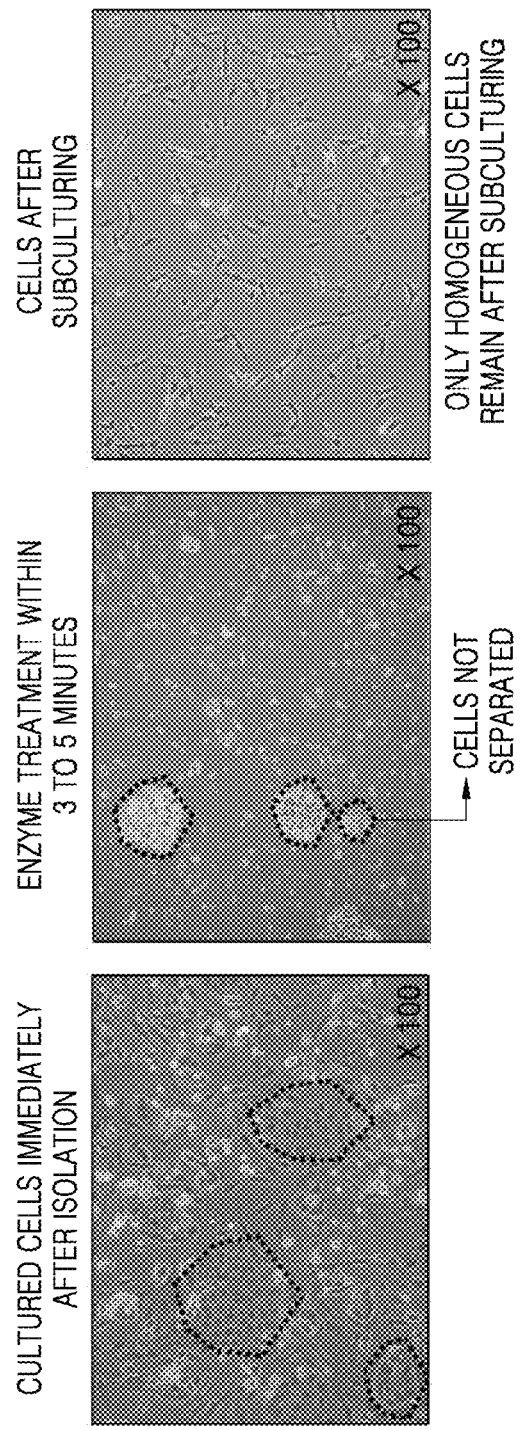

|       | SVF (IMMEDIATELY AFTER ISOLATION) | P1 (AFTER SUBCULTURING) |
|-------|-----------------------------------|-------------------------|
| CD44  | 2.22                              | 98.39                   |
| CD73  | 94.87                             | 99.58                   |
| CD90  | 1.13                              | 99.24                   |
| CD105 | 0.77                              | 91.35                   |
| CD45  | 0.36                              | 0.62                    |

… 
POSTNATAL ADHERENT CELLS AND PREPARATION METHOD THEREFOR

TECHNICAL FIELD

The present disclosure relates to enhanced postnatal adherent cells and a preparation method thereof.

BACKGROUND ART

A cell therapeutic agent is a drug used for the purpose of preventing or treating a specific disease through changing characteristics of cells by a method of proliferating or selecting cells ex vivo in order to restore functions of cells and tissues, and has recently received much attention in the fields of refractory diseases and regenerative medicines. Mesenchymal stem cells are multipotent stem cells that have self-renewal capacity and can differentiate into various lineages. Mesenchymal stem cells are also called "mesenchymal progenitor cells". Mesenchymal stem cells can differentiate into bones, fats, cartilages, nerves, muscles, bone marrow stromal cells, etc. according to conditions, and therefore, they have various therapeutic efficacies. Mesenchymal stem cells are a kind of adult stem cells, and may be mainly isolated together with hematopoietic stem cells from bone marrow. Mesenchymal stem cells are characterized by adhering to culture dishes, unlike hematopoietic stem cells that are floating in culture. Mesenchymal stem cells isolated and cultured under the culture conditions have been used in various experiments and/or clinical applications. However, mesenchymal stem cells have been isolated mainly from bone marrow, fat, or cord blood to be used in study, and during the extraction and isolation of bone marrow-derived mesenchymal stem cells, donors may suffer from pains and there is a disadvantage that a separation efficiency of mesenchymal stem cells is low.

Meanwhile, a placenta is a tissue discarded after birth, and therefore, is easy to obtain, and is an organ where many different kinds of adherent cells exist. Various cells such as mesenchymal stem cells, decidua cells, trophoblast cells, amniotic cells, endothelial cells, etc. are present in portions of the placenta. Zhang et al. disclose a method of isolating mesenchymal progenitor cells from placenta and characteristics of the isolated mesenchymal progenitor cells (Experimental Hematology 32 (2004) 657-664). According to this paper, amniotic sac and decidua are removed from a placenta, and then the placenta is washed with a phosphate buffered saline, and an irrigating solution and a culture solution are allowed to flow through arterial-vein circuit to remove residual blood from the tissues. The tissues are immersed in the culture solution for 12 hours to 24 hours, and mononuclear cells are obtained using a Ficoll density gradient and resuspended in a fetal bovine serum-containing medium, thereby obtaining mesenchymal progenitor cells. This method may be performed at a laboratory scale, because it requires complicated procedures, including Ficoll density-gradient separation. Moreover, since mesenchymal stem cells are cultured in the placenta itself for a long time, mixing of mononuclear cells present in the placenta may be caused. In addition, it is difficult to stably isolate/purify a large amount of healthy mesenchymal stem cells, making it difficult to clinically apply the mesenchymal stem cells. Furthermore, since the placenta free from amniotic sac and decidua is used in the method, the purity of mesenchymal progenitor cells may be lowered since the mesenchymal progenitor cells may be mixed with other cells derived from placental villi. Stable supply and acquisition of a sufficient number of cells which may show efficacy enough to be used as therapeutic agents are a prerequisite for the study of cell therapeutic agents. There is an urgent need to study methods of preparing cell populations applicable not only to existing stem cells but also to treatment and regeneration.

Considering ethical limitations to the research and utilization regarding isolation of cells which may be used as cell therapeutic agents, the limited number of cells to be isolated, and the types of cells that can be isolated from limited single tissues, it is very important to establish a method of isolating cells having excellent therapeutic effects which may be used as a cell therapeutic agent. However, as described above, the known method of isolating placenta-derived cells has a disadvantage of a low separation efficiency, and accordingly, there is a demand for a method of isolating new adherent cells which may be applicable to cell therapeutic agents while satisfying both proliferation capacity and differentiation capacity of placenta-derived cells, as an alternative to the known method.

DETAILED DESCRIPTION OF THE INVENTION

Technical Problem

An aspect provides a method of preparing postnatal adherent cells, the method including obtaining a placenta-derived tissue from a detached placenta; harvesting cell populations by adding an enzyme mixed solution to the placenta-derived tissue; isolating postnatal adherent cells by culturing the harvested cell populations in a container by adhesion culture and then treating the cell populations with an animal component-free (ACF) recombinant enzyme; and subculturing the isolated postnatal adherent cells under a hypoxia condition lower than a normoxia condition of 21% in a medium containing fibroblast growth factor-4 (FGF-4) and heparin.

Another aspect provides a method of increasing a preparation efficiency of postnatal adherent cells, the method including harvesting cell populations by adding an enzyme mixed solution to a detached placenta-derived tissue; isolating postnatal adherent cells by culturing the harvested cell populations in a flask by adhesion culture and then treating the cell populations with an animal component-free (ACF) recombinant enzyme; and subculturing the isolated postnatal adherent cells under a hypoxia condition lower than a normoxia condition of 21% in a medium containing fibroblast growth factor-4 (FGF-4) and heparin.

Technical Solution

An aspect provides a method of preparing enhanced postnatal adherent cells by isolating enhanced postnatal adherent cells (ePACs) from a placenta-derived tissue of a detached placenta and then culturing the cells.

The method of preparing enhanced postnatal adherent cells includes obtaining a placenta-derived tissue from a detached placenta; harvesting cell populations by adding an enzyme mixed solution to the placenta-derived tissue; isolating postnatal adherent cells by culturing the harvested cell populations in a container by adhesion culture and then treating the cell populations with an animal component-free (ACF) recombinant enzyme; and subculturing the isolated postnatal adherent cells under a hypoxia condition lower than a normoxia condition of 21% in a medium containing fibroblast growth factor-4 (FGF-4) and heparin.

The term "placenta", as used herein, refers to an organ that develops for a fetus during pregnancy of a mammal, and in a specific embodiment, the placenta may be a human placenta. One side of the placenta is in contact with the mother body, and the other side is in contact with the fetus, and the space therebetween is filled with the mother's blood, which supply the fetus with nutrients. Placenta consists of three layers of amnion, chorion, and decidua, and includes umbilical cord. Amnion is a clear membrane surrounding a fetus and containing amniotic fluid. Deciduas is a membrane formed as a result of a process in which the epithelial cells of the uterus are modified so that a fertilized egg becomes implanted in the uterine wall. Chorion is a membrane between amnion surrounding a fetus or amniotic fluid and deciduas, and develops from a fertilized egg to constitute a part of egg membrane. Umbilical cord is an organ that connects the fetus and the placenta, where exchange of materials between the mother and fetus takes place, and is connected to the fetus' heart through the navel.

The term "enhanced postnatal adherent cells (ePACs)", as used herein, refer to cells that have a fibroblast shape, proliferate unlimitedly, and have ability to differentiate into cell lineages such as adipocytes, osteocytes, or chondrocytes. The ePACs also refer to cells that are not derived from inner cell mass of blastocysts. The postnatal adherent cells from the human placenta detached from the body include, for example, (1) amniotic epithelial cells, (2) amnion-derived adherent cells, (3) chorion-derived adherent cells, (4) chorionic trophoblastic cells, and (5) umbilical cord cells.

The placenta may be a placenta separated and discarded from a healthy woman after birth. That is, the "detached placenta" refers to a placenta separated from the body of a woman after birth. The detached placenta may be promptly stored in a sterilized bag placed in an ice bath. The obtaining of the placental tissue from the detached placenta may be performed by a common anatomical method, e.g., by cutting the placental tissues present in the placenta into several parts with sterilized scissors. The placental tissues thus obtained are washed twice or more with phosphate buffered saline (PBS) containing an antibiotic (e.g., penicillin, streptomycin, gentamycin, etc.) to remove contaminants present in the tissues. In the present disclosure, the placental tissue may be an amniotic, chorionic, or decidual tissue. When the placental tissue is amnion, amnion may be obtained by pulling and peeling the chorionic plate membrane from the detached placenta and by scraping the separated chorionic plate membrane to remove chorion.

The collected placental tissue may be directly treated with enzymes or divided into small pieces using sterilized scissors, etc., and then treated with enzymes. For example, the placental tissue was divided into smaller pieces (e.g., about 5 mm or less) using sterilized scissors, etc., and then the divided cells may be treated with enzymes.

The enzyme mixed solution may be an enzyme mixture of various kinds of enzymes or an enzyme reaction solution, and the enzyme mixed solution reacting with the placental tissue may dissolve the tissue to separate adherent cells from the tissue. The enzyme mixed solution may include collagenase, trypsin, and dispase, and the enzyme mixed solution may include water or saline containing collagenase, trypsin, and dispase, for example, Hank's balanced salt solution (HBSS). The collagenase may refer to an enzyme that cleaves peptide bonds of collagen, and may include collagenase type I, type II, type III, type IV, or a combination thereof. Further, the enzyme mixed solution may further include DNA hydrolase (deoxyribonuclease, DNase) I or II. A concentration of collagenase in the enzyme mixed solution may be, for example, 0.5 mg/ml to 5 mg/ml, 0.5 mg/ml to 3 mg/ml, 0.8 mg/ml to 2 mg/ml, or 0.8 mg/ml to 1.5 mg/ml, and in a specific embodiment, 1.2 mg/ml. A concentration of trypsin in the enzyme mixed solution may be, for example, 1 mg/ml to 5 mg/ml, 1 mg/ml to 3 mg/ml, 1.5 mg/ml to 2.5 mg/ml, or 1.5 mg/ml to 2 mg/ml, and in a specific embodiment, 1.8 mg/ml. A concentration of dispase in the enzyme mixed solution may be, for example, 0.1 U/ml to 5 U/ml, 0.1 U/ml to 3 U/ml, 0.5 U/ml to 2.5 U/ml, or 0.5 U/ml to 1.5 U/ml, and in a specific embodiment, 1 U/ml. A concentration of DNA hydrolase in the enzyme mixed solution may be, for example, 0.001 mg/ml to 1 mg/ml, 0.001 mg/ml to 0.5 mg/ml, 0.01 mg/ml to 0.25 mg/ml, or 0.01 mg/ml to 0.05 mg/ml, and in a specific embodiment, 0.025 mg/ml.

In a specific embodiment, reaction of the tissue and the enzyme mixed solution may be allowed under shaking, and the shaking may be performed at about 20° C. to 40 about ° C., about 30° C. to about 40° C., or about 35° C. to about 40° C., for example, at about 37° C. for about 5 minutes to about 60 minutes or about 10 minutes to about 30 minutes, for example, for about 10 minutes to about 30 minutes twice.

Additionally, after reaction of the tissue and the enzyme mixed solution, a process of inactivating the enzyme reaction solution may be further performed, and for example, the enzymatic reaction may be terminated by adding FBS. Further, a method of isolating tissue cells, for example, amniotic cells (that is, adherent cells) from the enzyme reaction solution may be performed by a common method known in the art. For example, after centrifugation, cells may be isolated by using a cell strainer.

The term "isolation of ePACs", as used herein, refers to isolation of cells having ability to differentiate into cell lineages such as adipocytes, osteocytes, or chondrocytes. Isolation of cell populations by treatment of tissues with the enzyme mixed solution may be used interchangeably with isolation of ePACs. That is, for example, isolation of amniotic cells may be used interchangeably with isolation of amnion-derived adherent cells. Screening of single cells of ePACs from the isolated placenta cells by using enzymes is well known in the art.

The isolated cell populations are adhered onto a container and then treated with an animal component-free recombinant enzyme to increase isolation purity of adherent cells. Adhesion culture (e.g., P0) of the isolated cell populations in a container (e.g., flask) may include culturing the cell populations in a cell culture medium, for example, in a medium to which fibroblast growth factor (FGF-4) and heparin are added. FGF-4 may be added to the medium at a concentration of about 10 ng/ml to about 40 ng/ml, or about 20 ng/ml to about 30 mg/ml, for example, at a concentration of 25 ng/ml. Heparin may be added to the medium at a concentration of about 0.5 µg/ml to about 2 µg/ml, or about 0.5 µg/ml to about 1.5 µg/ml, for example, at a concentration of 1 µg/ml. The medium may further include, for example, fetal bovine serum, and an antibiotic (e.g., penicillin, streptomycin, gentamicin, etc.). In a specific embodiment, a PS-CM medium containing 10% fetal bovine serum, 50 µg/ml of gentamicin, 1 µg/ml of heparin, and 25 ng/ml of FGF-4 may be used. Culture of the cell populations may be performed under a hypoxia condition. The term "hypoxia" means an oxygen partial pressure lower than an oxygen partial pressure of 21% which is a general normoxia condition. The hypoxia condition may be a condition having an oxygen partial pressure of 1% to 15%, 1% to 12%, 1% to 10%, or 1% to 5%, for example, 1%, 2%, 3%, 4%, 5%, 6%, 7%, 8%, or 9%. The culture may be performed, for example, for 2 days to 7 days, or for 3 days to 5 days, and after culture, the animal component-free recombinant enzyme may be treated thereto.

The term "animal component-free enzyme", as used herein, means that the enzyme is originated from a non-animal, which means that the enzyme is not purified from an animal supply source. The animal component-free enzyme may be originated from recombination, for example, originated from bacteria, yeasts, or plants. The enzyme originated from recombination may mean any enzyme produced by recombinant DNA technology including use of microorganisms, for example, bacteria, viruses, yeasts, plants, etc. The enzyme may be animal component-free recombinant trypsin, for example, recombinant trypsin produced in corn. The animal component-free recombinant trypsin is commercially available, and for example, it may be TrypLE™ Select (GIBCO Invitrogen), TrypLE™ Express (GIBCO Invitrogen), TrypZean™ (Sigma Aldrich), or Recombinant Trypsin Solution™ (Biological Industries).

In the method of preparing ePACs according to a specific embodiment, a passage number of the subculturing is not particularly limited, and the passage number may be appropriately selected according to the desired number of proliferating cells. Commonly, the passage number may be at least 1 passage or more, or 10 passages or more. For example, 1 passage to 20 passages, 1 passage to 6 passages, 1 passage, 3 passages, or 6 passages may be performed to obtain the clinically required cumulative number of proliferating cells.

The method of preparing ePACs according to a specific embodiment of the present invention includes subculturing ePACs obtained as above in a cell culture medium, for example, in a medium to which fibroblast growth factor (FGF-4) and heparin are added. The medium to which fibroblast growth factor (FGF-4) and heparin are added, and culture conditions are the same as described above. Further, upon subculturing, treatment of the animal component-free recombinant enzyme may be also additionally performed as described above. That is, at every stage of subculturing before subculturing of the cells to the next stage, the cells were treated with the animal component-free recombinant enzyme and harvested to increase purity of the adherent cells. For example, the animal component-free recombinant enzyme may be treated before transferring the cells for P2 at the stage from P1 to P2.

At least about 20%, about 25%, about 30%, about 35%, about 40%, about 45%, about 50%, about 55%, about 60%, about 65%, about 70%, about 75%, about 80%, about 85%, about 90%, about 95%, about 98%, or about 99% of ePACs prepared in the present invention may express CD44, CD73, CD90 and CD105 positive surface markers which are adherent cell markers expressed on the cell surface during cell differentiation•proliferation, and at least about 70% or less, at least about 60% or less, at least about 50% or less, at least about 40% or less, at least about 30% or less, at least about 20% or less, at least about 10% or less, at least about 5% or less, or at least about 1% or less thereof may express CD45 negative surface marker which is a hematopoietic cell marker. The term "positive", as used herein, with respect to a cell marker, means that the cell marker exists in a large amount or a high concentration, as compared with that in other cells as a reference. That is, any marker is present inside or on the surface of a cell, and therefore, if a cell may be distinguished from one or more other cell types by using the marker, the cell may be positive for the marker. Further, the term "positive" means that cells have signals of higher intensity that a background intensity, for example, cells have the marker in an amount enough to be detectable in a cell-measuring device. For example, cells may be detectably labeled with CD105-specific antibodies, and when signals from these antibodies are detectably stronger than those of a control (e.g., background intensity), the cells are "CD105$^+$". The term "negative", as used herein, means that although antibodies specific to a particular cell surface marker are used, the marker cannot be detected, as compared with the background intensity. For example, if a cell cannot be detectably labeled with a CD45-specific antibody, the cell is "CD45$^-$".

In the method of preparing ePACs according to a specific embodiment of the present invention, harvesting of the cell populations may increase yield of ePACs to, for example, 50 times or higher by using the enzyme mixed solution, compared with yield in a method of not using the enzyme mixed solution.

In the method of preparing ePACs according to another specific embodiment of the present invention, treatment of the animal component-free recombinant enzyme may not separate dense cell masses and may remain only homogeneous cells after subculturing.

In the method of preparing ePACs according to still another specific embodiment, ePACs may be cultured under a hypoxia condition in the culturing of ePACs, so as to decrease a double time of the cells, thereby increasing a cell proliferation rate to, for example, 7 times or more.

The ePACs prepared by the method of preparing ePACs according to a specific embodiment may release proteins described in the following Table 3. In particular, ePACs may release vascular endothelial growth factor (VEGF), transforming growth factor (TGF)-β1, hepatocyte growth factor (HGF), interleukin (IL-6), or progranulin which is specifically effective for neurological diseases. Further, according to another specific embodiment, ePACs have a remarkable ability to migrate to damaged tissues. Therefore, ePACs may be used as a cell therapeutic agent in the treatment of neurological diseases and other diseases on which the above secretory proteins may effectively act.

Another aspect provides a method of increasing a preparation efficiency of ePACs, the method including harvesting cell populations by adding an enzyme mixed solution to a detached placenta-derived tissue; isolating ePACs by culturing the harvested cell populations in a flask by adhesion culture and then treating the cell populations with an animal component-free (ACF) recombinant enzyme; and subculturing the isolated ePACs under a hypoxia condition lower than a normoxia condition of 21% in a medium containing fibroblast growth factor-4 (FGF-4) and heparin.

The method of preparing ePACs is the same as described above.

In the present disclosure, the "increasing of the preparation efficiency of ePACs" means increasing of yield of the cells, increasing of a proliferation rate, or increasing of purity of the cells, as compared with a method of preparing ePACs in the same manner excluding performing the method of the above-described step. For example, the increasing of the preparation efficiency of ePACs means increasing of yield of adherent cells, as compared with a method of not using the enzyme mixed solution, increasing of a proliferation rate of adherent cells, as compared with a method under a normoxia condition, or increasing of purity of adherent cells, as compared with a method of not using the animal component-free recombinant enzyme.

Further, the increasing of the preparation efficiency may include not only increasing of efficiency of the preparation method itself but also increasing of useful characteristics of the prepared adherent cells, for example, may include increasing of production of proteins useful in the treatment of the above-described diseases or increasing of the ability to migrate to damaged tissues.

Still another aspect provides ePACs which are prepared by the method of preparing ePACs including obtaining a placenta-derived tissue from a detached placenta; harvesting cell populations by adding an enzyme mixed solution to the placenta-derived tissue; isolating ePACs by culturing the harvested cell populations in a container by adhesion culture and then treating the cell populations with an animal component-free (ACF) recombinant enzyme; and subculturing the isolated enhanced postnatal adherent cells under a hypoxia condition lower than a normoxia condition of 21% in a medium containing fibroblast growth factor-4 (FGF-4) and heparin.

The method is the same as described above.

At least about 20%, about 25%, about 30%, about 35%, about 40%, about 45%, about 50%, about 55%, about 60%, about 65%, about 70%, about 75%, about 80%, about 85%, about 90%, about 95%, about 98%, or about 99% of the ePACs prepared by the method may express CD44, CD73, CD90 and CD105 positive surface markers which are adherent cell markers expressed on the cell surface, and at least about 70% or less, at least about 60% or less, at least about 50% or less, at least about 40% or less, at least about 30% or less, at least about 20% or less, at least about 10% or less, at least about 5% or less, or at least about 1% or less thereof may express CD45 negative surface marker which is a hematopoietic cell marker. Further, ePACs prepared by the method may release proteins described in the following Table 3 and have an increased ability to migrate to damaged tissues.

Still another aspect provides a cell therapeutic agent or a pharmaceutical composition including ePACs.

Still another aspect provides a method of preventing or treating a disease, the method including administering ePACs or the cell therapeutic agent or the pharmaceutical composition including the same to a subject in need thereof.

Still another aspect provides use of ePACs in the preparation of a drug for preventing or treating a disease.

ePACs according to a specific embodiment may release proteins that are advantageous for disease treatment as described above and have a remarkable ability to migrate into damaged tissues. Therefore, ePACs may be usefully applied to a cell therapy agent or a pharmaceutical composition for the prevention or treatment of various diseases.

Examples of the diseases may include neurological diseases, liver diseases, or metabolic diseases. Examples of the neurological diseases may include Alzheimer's disease, chronic or acute stroke, cerebral infarction, brain tumor, cerebral edema, brain ischemia, multiple sclerosis, frontotemporal dementia, progressive supranuclear palsy, corticobasal degeneration, Pick's disease, or dementia pugilistica (DP). Examples of the metabolic diseases may include obesity, type 1 or 2 diabetes, dyslipidemia, insulin resistance, hepatic steatosis, or non-alcoholic fatty liver.

A dosage of the cell therapeutic agent or the pharmaceutical composition according to a specific embodiment may be $1.0 \times 10^3$ to $1.0 \times 10^{10}$ cell/kg (body weight) or subject, or $1.0 \times 10^7$ to $1.0 \times 10^8$ cell/kg (body weight) or subject, based on the adherent cells. However, the dosage may be variously prescribed depending on various factors such as a formulation method, an administration mode, a patient's age, body weight, sex, disease conditions, diet, an administration time, an administration route, an excretion rate, and reaction sensitivity, and those skilled in the art may appropriately adjust the dosage, considering these factors. Administration frequency may be once or twice or more within the clinically allowable range of side effects, and administration may be given to one site or two or more sites. The dosage per kg or per subject for non-human animals may be the same as that for humans, or may be converted from the above-described dosage, for example, based on a volume ratio (e.g., mean value) between organs (heart, etc.) of the human and animal subjects. Animals to be treated according to a specific embodiment may be exemplified by humans and other desired mammals, and specifically, may include humans, monkeys, mice, rats, rabbits, sheep, cows, dogs horses, pigs, etc.

The cell therapeutic agent or the pharmaceutical composition according to a specific embodiment may include the adherent cells and pharmaceutically acceptable carriers and/or additives as an active ingredient, and for example, may include sterilized water, physiological saline, a standard buffer (e.g., phosphoric acid, citric acid, or other organic acids), a stabilizer, a salt, an antioxidant (e.g., ascorbic acid, etc.), a surfactant, a suspending agent, an isotonic agent, a preservative, etc. For local administration, the cell therapeutic agent or the pharmaceutical composition is preferably combined with an organic substance such as a biopolymer, an inorganic substance such as hydroxyapatite, specifically, collagen matrix, a polymer or copolymer of polylactic acid, a polymer or copolymer of polyethylene glycol, and chemical derivatives thereof. When the cell therapeutic agent or the pharmaceutical composition according to a specific embodiment is prepared in an injectable formulation, cell populations may be dissolved in a pharmaceutically acceptable carrier or may be frozen in a solution state in which the cell populations are dissolved.

The cell therapeutic agent or the pharmaceutical composition according to a specific embodiment may include, if necessary, a suspending agent, a solubilizing aid, a stabilizer, an isotonic agent, a preservative, an adsorption inhibitor, a surfactant, a diluent, an excipient, a pH adjuster, an analgesic agent, a buffer, a reducing agent, an antioxidant, etc., depending upon the administration mode and formulation. In addition to those described above, pharmaceutically acceptable carriers and agents suitable in the present disclosure are described in detail in a literature [Remington's Pharmaceutical Sciences, $19^{th}$ ed., 1995].

The cell therapeutic agent or the pharmaceutical composition according to a specific embodiment may be formulated in a unit dosage form or into a multidose container using a pharmaceutically acceptable carrier and/or excipient according to a method that may be easily carried out by those skilled in the art to which the present disclosure pertains. In this regard, the formulation may be in a form of a solution, a suspension, or an emulsion in an oily or aqueous medium, a powder, granules, a tablet, or a capsule.

Advantageous Effects of the Invention

According to a method of isolating and culturing enhanced postnatal adherent cells according to an aspect, purity, yield, and a proliferation rate of adherent cells from placental tissues may be increased, and adherent cells which secrete proteins effective for neurological diseases and have an improved ability to migrate to damaged tissues may be prepared. In particular, the adherent cells of the present invention retain high differentiation capacity and proliferation capacity, thereby maintaining characteristics suitable for cell therapeutic agents.

DESCRIPTION OF THE DRAWINGS

FIGS. 1A and 1B show homogeneity and surface antigen properties of a method of preparing adherent cells according to a specific embodiment;

MODE OF THE INVENTION

Figure 1B:
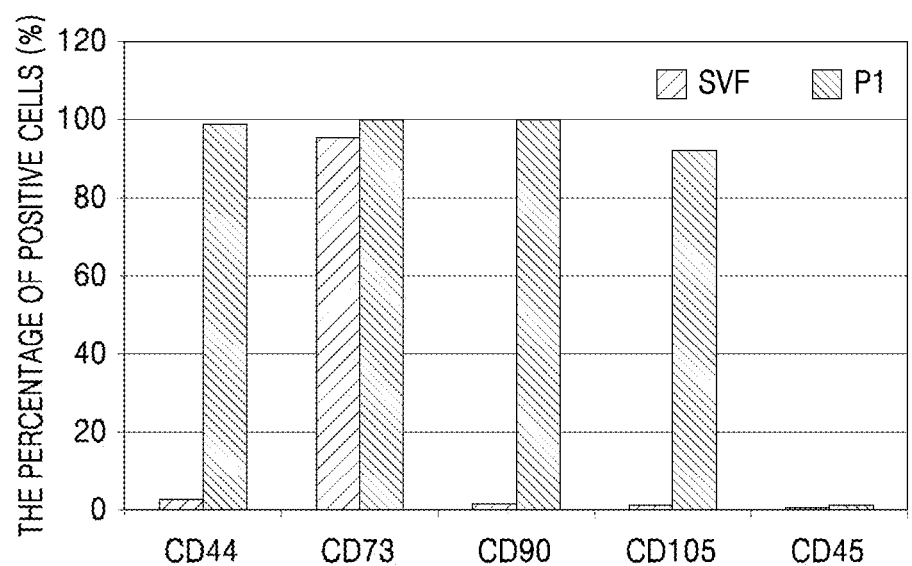

Hereinafter, the present invention will be described in more detail. However, these Examples are for illustrative purposes only, and the scope of the present invention is not intended to be limited by these Examples.

Example 1: Method of Preparing Enhanced Postnatal Adherent Cells

1. Isolation of Adherent Cells from Amniotic Tissue of Placenta and Culture Thereof After an informed consent form was signed by a healthy woman who had normally delivered, a chorionic plate membrane was pulled and peeled off from a placental tissue collected during normal placenta delivery. The removed chorionic plate membrane was washed with Ca/Mg free DPBS containing gentamicin twice or five times to remove blood, and then a chorionic plate was scraped and removed by using a slide glass. The remaining amnion was divided into pieces as small as possible using surgical scissors such that the pieces was in a size of about 1 mm to about 5 mm, and 20 ml of an enzyme reaction solution (enzyme mixture) was added to the small tissue pieces and allowed to react in a shaking incubator at 37° C. and 200 rpm for 15 minutes. To inactivate the enzyme reaction solution, 2 ml of FBS was added at a ratio of 1:10, and the reaction solution was centrifuged at 1,500 rpm for 3 minutes, and then a supernatant was transferred to a new tube. This procedure was repeated twice with respect to the remaining tissues. From the dissolved tissue, amniotic cells were isolated using a 100-μm cell strainer.

The isolated amniotic cells were centrifuged and a supernatant was removed therefrom. Cell pellets were suspended in a medium supplemented with FGF4 and heparin (PS-CM medium), and seeded in a T-flask, and then cultured at 37° C. under a hypoxia condition ($CO_2$ 5%, $O_2$ 3%). The cells were cultured until cell colonies were formed to occupy 50%~80% of the bottom area of T-flask. Every 3 days to 4 days, PS-CM medium (medium containing FGF, heparin, and FBS) was replaced to remove cells which did not adhere to the bottom of flask. Only cells isolated by treatment of TrypLE, which is an animal component-free (ACF) recombinant enzyme (Invitrogen), in a 37° C. incubator for a short time (3 minutes) at a first passage, were used to increase purity of amnion-derived adherent cells.

Components of the enzyme reaction solution (enzyme mixture) used above and components of PS-CM medium are shown in the following Tables 1 and 2, respectively.

TABLE 1

| Components of enzyme reaction solution | | |
|---|---|---|
| Component | Concentration | Available source |
| HBSS (Hank's Balanced Salt Solution) | — | Invitrogen |
| Trypsin | 1.8 mg/ml | Sigma |
| Dispase | 1 U/ml | Invitrogen |
| Collagenase I | 1.2 mg/ml | Invitrogen |
| DNA hydrolase (DNase) I | 25 μg/ml | Rhoche |

TABLE 2

| Components of PS-CM medium | | |
|---|---|---|
| Component | Concentration | Available source |
| MEM alpha GlutaMAX | — | Invitrogen |
| Fetal bovine serum (FBS) | 10% | Invitrogen |
| Fibroblast growth factor 4(FGF4) | 25 ng/ml | Peprotech |
| Heparin | 1 μg/ml | Sigma |
| Gentamicin | 50 μg/ml | Invitrogen |

Cell populations isolated during the preparation process of the amnion-derived adherent cells were cultured, and then treated with animal component-free enzyme, followed by subculturing. Cells were observed under an inverted microscope (Eclipse TS100 (Nikon)) at 100× magnification, and result is shown in FIG. 1A. Further, in order to analyze characteristics of the prepared amnion-derived adherent cells, $1 \times 10^6$ cells were collected in a 1.5-ml tube, and stained with anti-CD44, anti-CD73, anti-CD90, anti-CD105, and anti-CD45, respectively and then analyzed with FACS caliber. Results are shown in FIG. 1B.

FIG. 1 shows homogeneity and surface antigen properties of a method of preparing adherent cells according to a specific embodiment.

As shown in FIG. 1A, it was confirmed that dense cell masses were not separated and only homogeneous cells remained after short-term treatment of animal component-free recombinant enzyme. As shown in FIG. 1B, cells positive for adherent cell markers were less than 10% immediately after isolation whereas cells positive for adherent cell markers were 90% or more and cells positive for CD45 was less than 1% after subculturing. These results suggest that the method of preparing the adherent cells according to a specific embodiment may be used to increase purity of the enhanced postnatal adherent cells.

2. Analysis of Yields of Amnion-Derived Adherent Cells According to Components of Enzyme Reaction Solution To analyze yields of amnion-derived adherent cells according to enzyme reaction solution which was prepared by mixing an HBSS solution with 1.2 mg/ml collagenase, 1.8 mg/ml trypsin, 25 ug/ml DNase, and 1 U/ml dispase as in the enzyme reaction solution of Table 1, three enzyme reaction solutions (a collagenase-excluded group, a dispase-excluded group, and a trypsin-excluded group) prepared by excluding each of 1.2 mg/ml collagenase, 1.8 mg/ml trypsin, and 1 U/ml dispase from the enzyme reaction solution) were used as comparative control groups.

In detail, each of the enzyme reaction solution of Table 1 and three enzyme reaction solutions of the comparative control groups was used to isolate adherent cells from an amniotic tissue of a placenta. To compare yields thereof, cells isolated by each of the enzyme reaction solutions were seeded in a T-flask and cultured at 37° C. under a hypoxia condition ($CO_2$ 5%, $O_2$ 3%). Every 3 days to 4 days, PS-CM medium was replaced to remove cells which did not adhere to the bottom of flask, and cells isolated by the enzyme reaction solution of Table 1 were cultured until cells formed colonies. Then, cells were separated from each T-flask, and the number of cells counted was converted to the number of cells per tissue weight (g) to confirm cell yield. Further, morphologies of the adherent cells separated by the enzyme reaction solutions were observed under an inverted microscope (Eclipse TS100 (Nikon)) at 40× magnification and results are shown in FIG. 2.

FIG. 2 show cell yields of the method of preparing adherent cells according to a specific embodiment depending on components of an enzyme reaction solution.

Figure 2A:
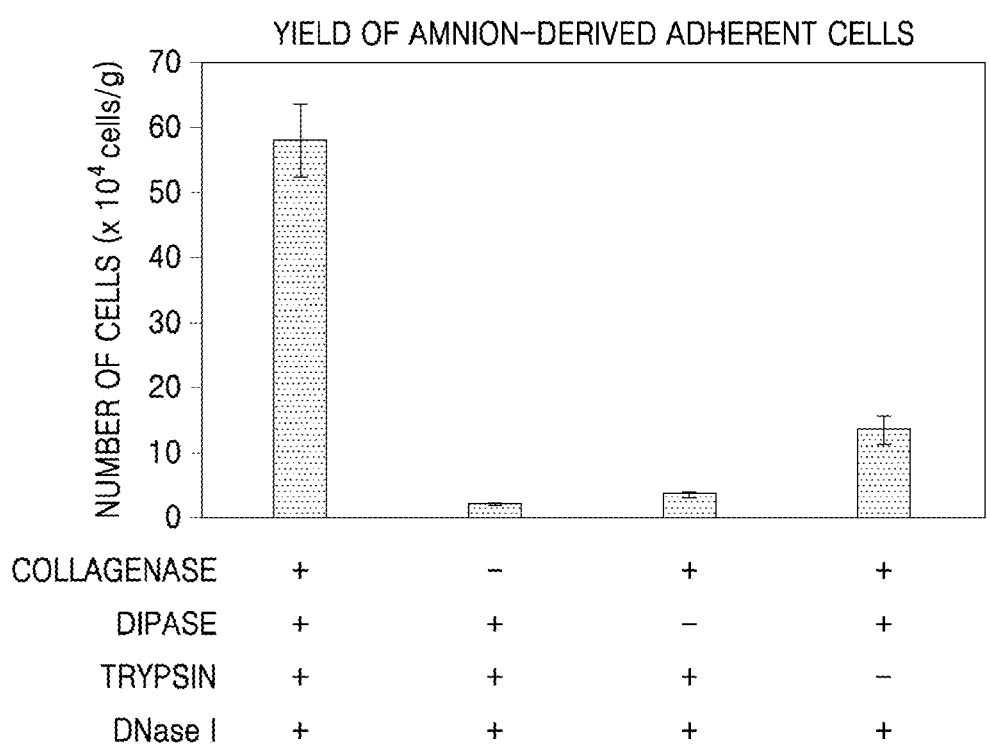
FIGS. 2A and 2B show cell yields of the method of preparing adherent cells according to a specific embodiment depending on components of an enzyme reaction solution.

As shown in FIG. 2A, the enzyme reaction solution of Table 1 showed remarkably high yield of amnion-derived adherent cells, as compared with the collagenase-excluded group, trypsin-excluded group, and dispase-excluded group, and in particular, showed about 50 times or more increased cell yield, compared with the collagenase-excluded group, and about 5 times to about 6 times or more increased cell yield, compared with the trypsin-excluded group.

Figure 2B:
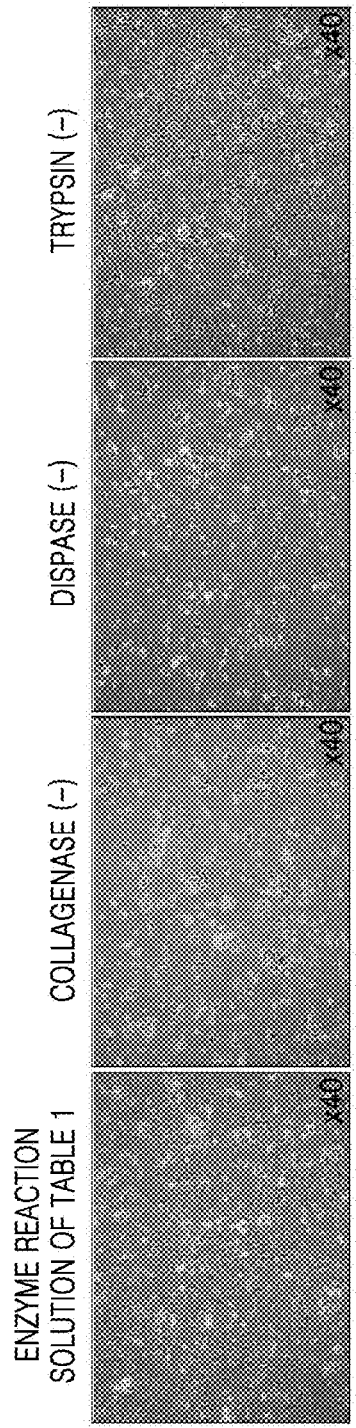

As shown in FIG. 2B, adherent cells isolated by using the enzyme reaction solution of Table 1 were composed of cells having fibroblast-specific morphology with irregular protrusions, as compared with the collagenase-excluded group, trypsin-excluded group, and dispase-excluded group.

3. Comparison of Adherent Cells According to Culture Conditions

To analyze characteristics of adherent cells according to culture conditions, adherent cells cultured under a hypoxia condition were compared with those cultured under a normoxia condition.

In detail, adherent cells were isolated and cultured under a normoxia condition in the same manner as in 1 of Example 1, except that a normoxia condition was employed instead of the hypoxia condition of 1 of Example 1. To compare the total numbers and doubling times of adherent cells subcultured for 1 passage to 19 passages (P1 to P19) under the hypoxia and normoxia conditions, each same number of cells was seeded in a 6-well plate, and cells were harvested when they occupied 70%~80% of the bottom area of the plate, and the number of cells was counted. Measurement was repeated total three times. 10 µl of cell suspension was mixed with 10 µl of trypan blue, and 10 µl thereof was used to count the total number of cells with a hemocytometer. The doubling time, which is a time it takes for a cell to double, was calculated using the total number of cells and the time when the number was measured. Further, to analyze cell's ability to migrate to damaged tissues, migration abilities of cells were examined by using a transwell. The equal number of cells was seeded on the upper part of a transwell, and then chemokine was added to a culture medium in the lower part. After culturing for several days, the number of cells that migrated through the transwell was counted to confirm cell migration, and results are shown in FIG. 3.

FIG. 3 shows comparison of characteristics according to culture conditions (under hypoxia or normoxia condition) of the method of preparing adherent cells according to a specific embodiment.

Figure 3A:
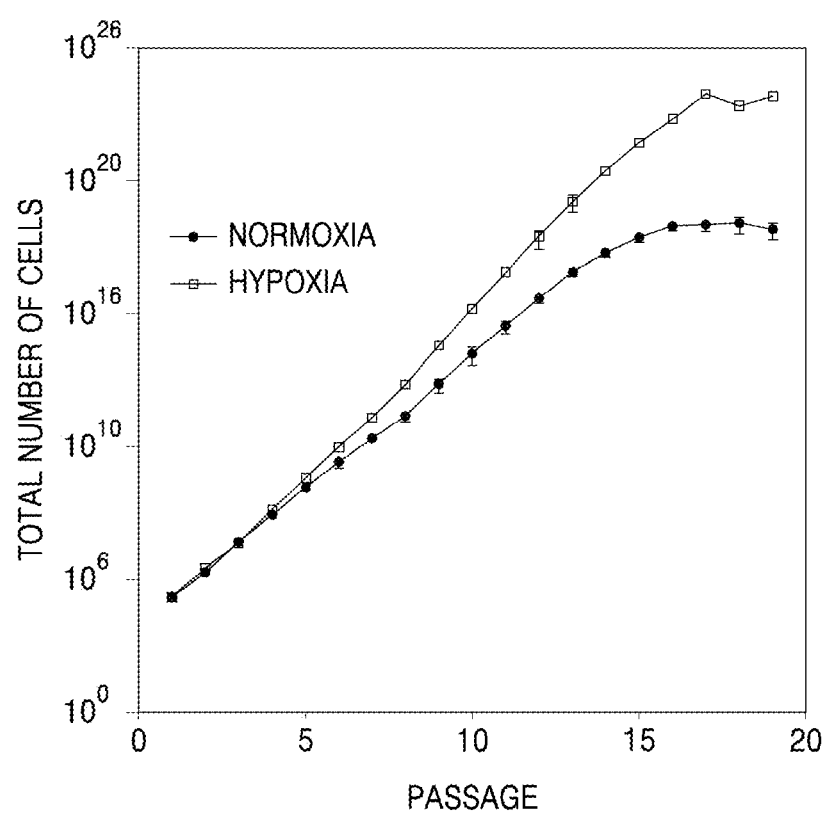
FIGS. 3A, 3B, and 3C show comparison of characteristics according to culture conditions (under hypoxia or normoxia condition) of the method of preparing adherent cells according to a specific embodiment.
Figure 3B:
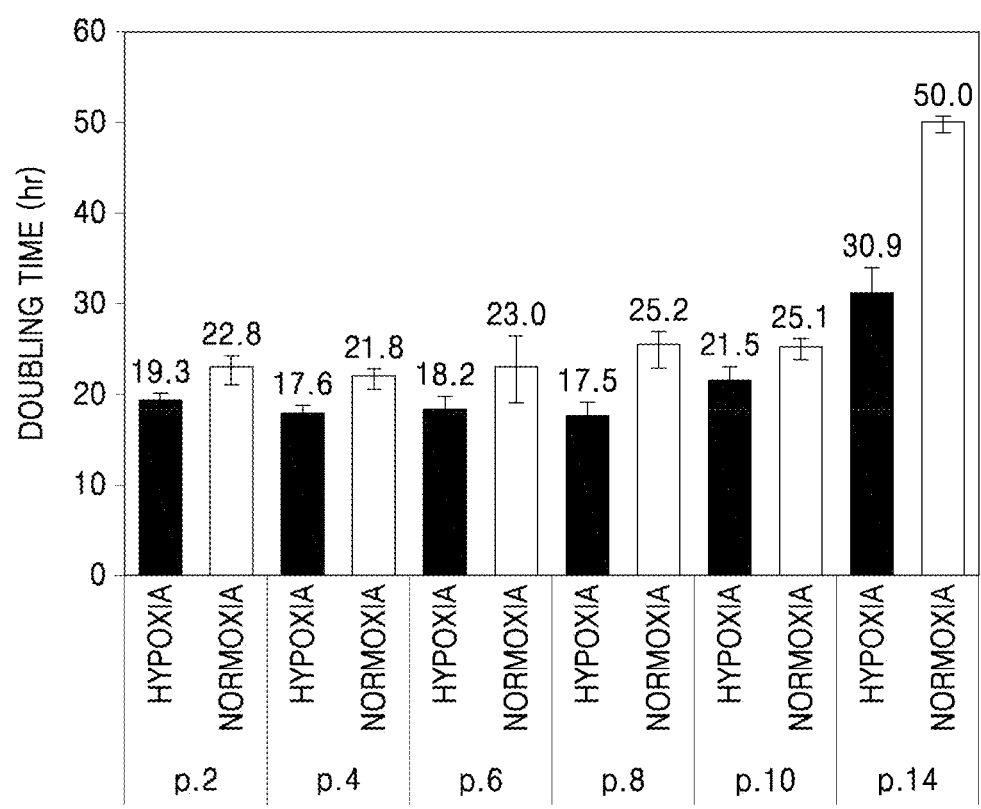

As shown in FIGS. 3A and 3B, as compared with cells cultured under the normoxia condition, cells cultured under the hypoxia condition showed a rapid cell proliferation rate of a short doubling time of about 20 hours, and as a result, the number of cells accumulated for the same period was remarkably increased by 7 times or more.

Figure 3C:
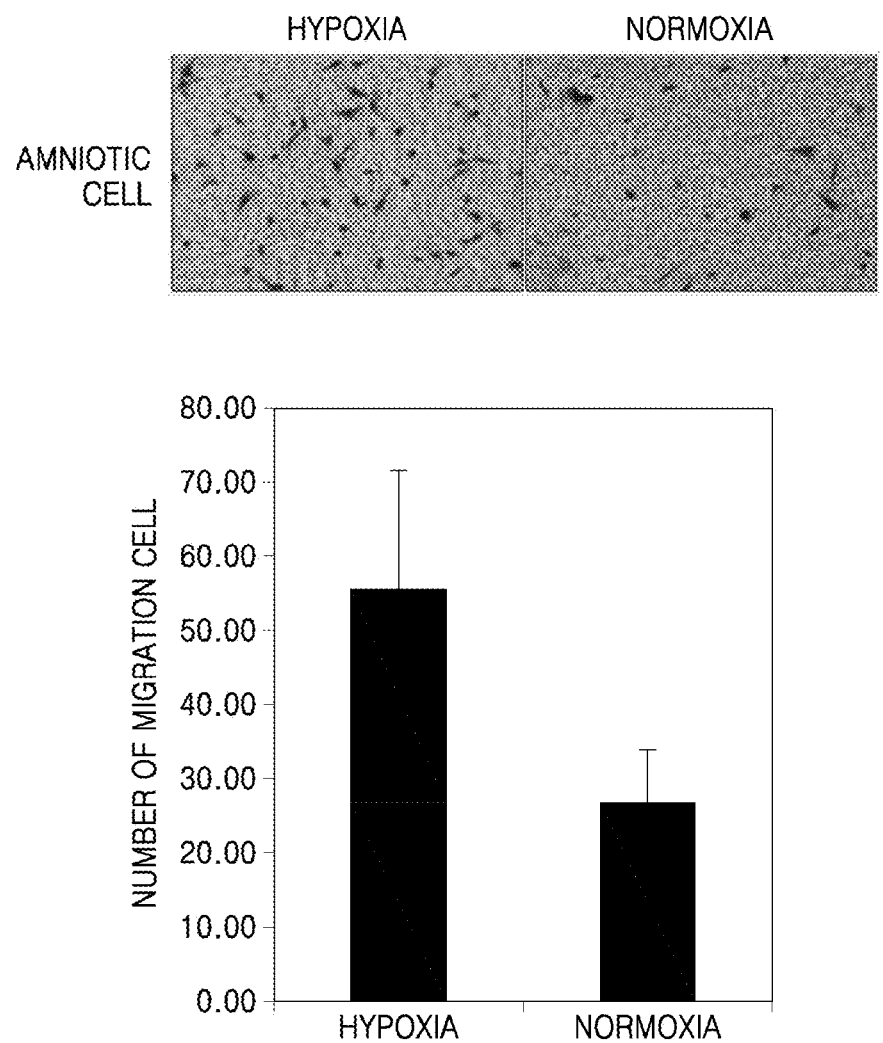

As shown in FIG. 3C, results of analyzing cell's ability to migrate to damaged tissues showed that cells cultured under the hypoxia condition have about twice or higher migration ability, as compared with cells cultured under the normoxia condition, suggesting that adherent cells cultured under the hypoxia condition have significant ability to migrate to damage tissue, thereby being usefully applied to cell therapeutic agents.

4. Analysis of Morphological Characteristics and Genetic Safety of Adherent Cells To examine genetic abnormality of the adherent cells prepared in 1 of Example 1, morphological characteristics and genetic safety thereof were analyzed.

In detail, in order to observe morphologies of adherent cells at P7 and P14, an inverted microscope (Eclipse TS100 (Nikon)) was used to examine cell morphology at 40× magnification. It was confirmed that cells have a morphology specific to spindle-shaped fibroblasts with irregular protrusions, and karyotyping was performed by G-banding (Gosden J R (1994) Chromosome analysis protocols. In: Walker J M (ed.), Methods in Molecular Biology, vol. 29. Totawa: Humana Press, Sumner A T (1990) Chromosome Banding. London: Unwin Hyman).

Chromosomal abnormalities of adherent cells at P1, P3, and P6 were analyzed by single nucleotide polymorphisms (SNPs). In detail, DNAs were extracted from cells at each passage by using a Promega DNA extraction kit, and used as samples. Illumina HumanOmni1-Quad Chip was used and iSCAN® scanner was used for measurement. First, each 400 ng of the DNA samples was amplified by whole genome amplification, and randomly fragmented by a chemical method, and purified by 2-propanol precipitation. The chip was pretreated with a buffer solution before applying the DNA sample thereto, and then the DNA sample was applied thereto. Next, incubation was performed for about 16 hours, and then staining, ASPE (allele specific primer extension), hybridization, target removal, and washing were performed. Then, scanning was performed by using IlluminaiScan, and data analysis was performed by using GenomeStudio® software.

Figure 4A:
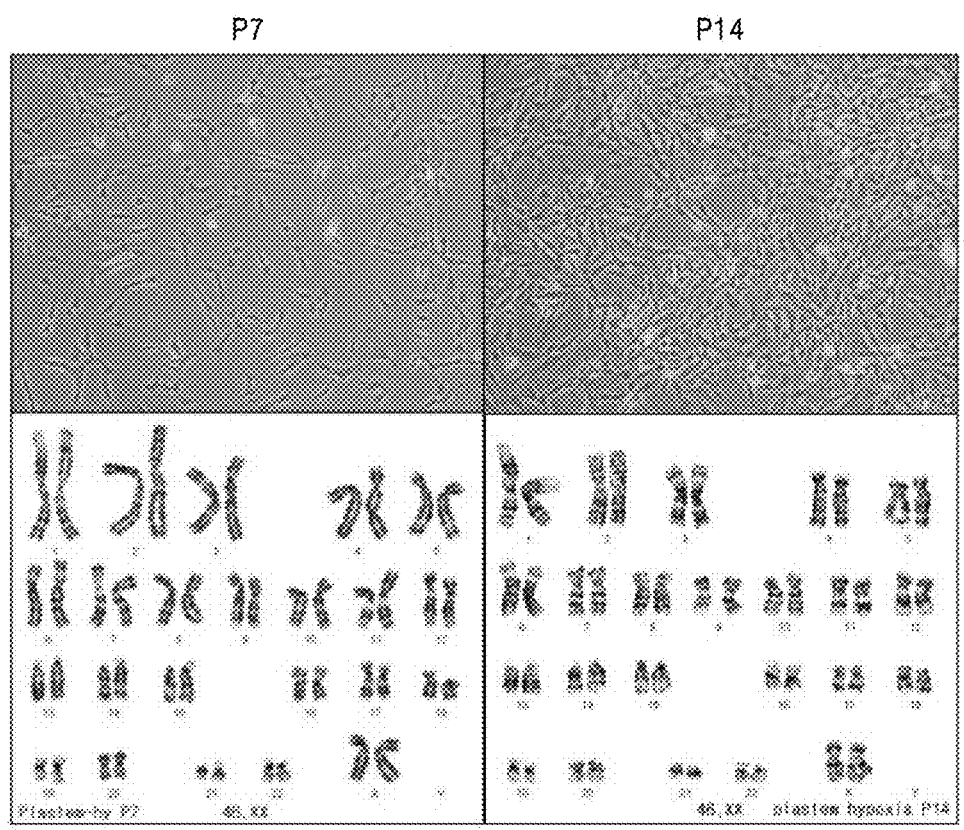
FIGS. 4A and 4B show morphological characteristics and genetic safety of adherent cells prepared by the method of preparing adherent cells according to a specific embodiment.
Figure 4B:
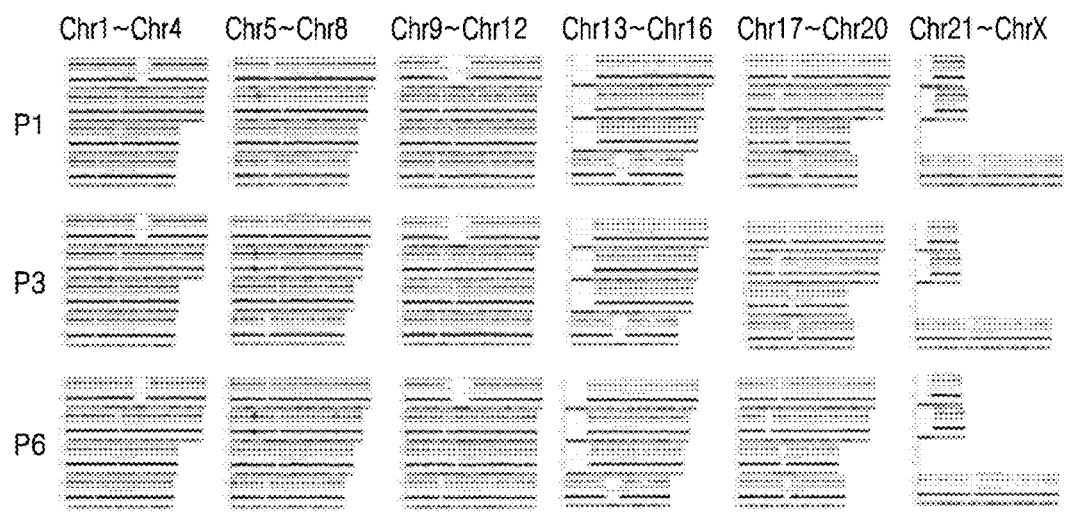
Figure 5A:
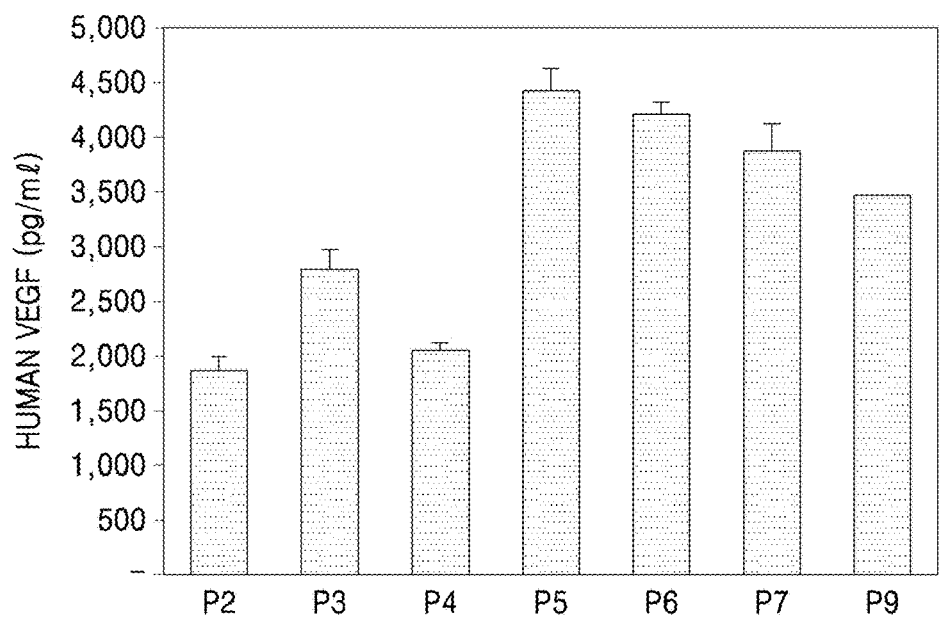
FIGS. 5A, 5B, 5C, 5D, and 5E show quantification result of proteins secreted by adherent cells according to subculturing of the adherent cells which were prepared by the method of preparing adherent cells according to a specific embodiment.
Figure 5B:
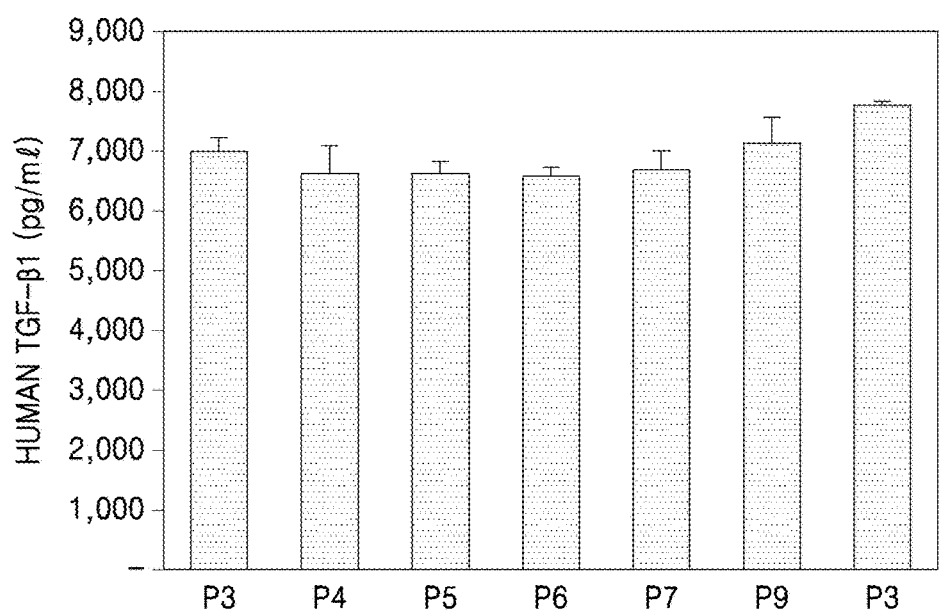
Figure 5C:
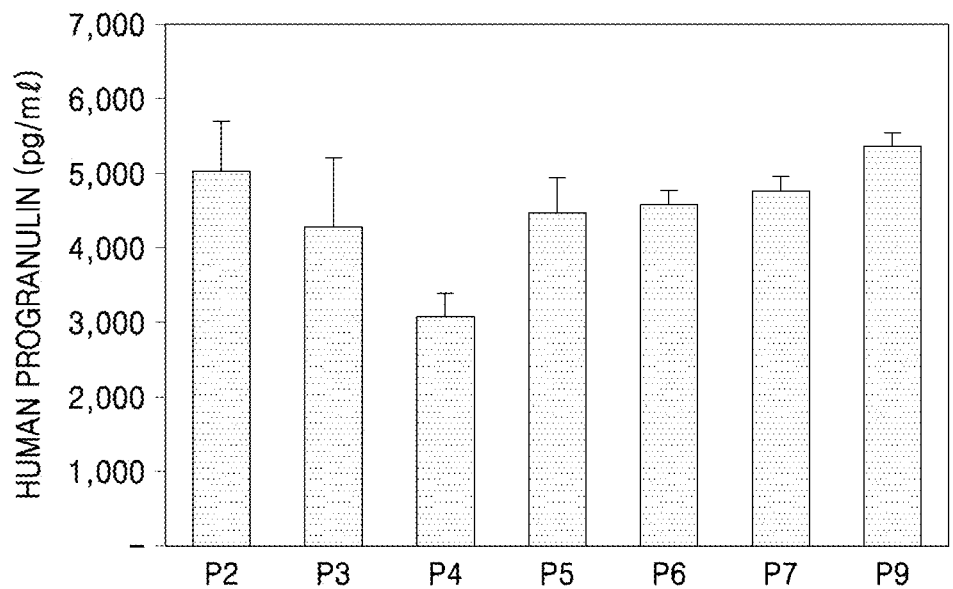
Figure 5D:
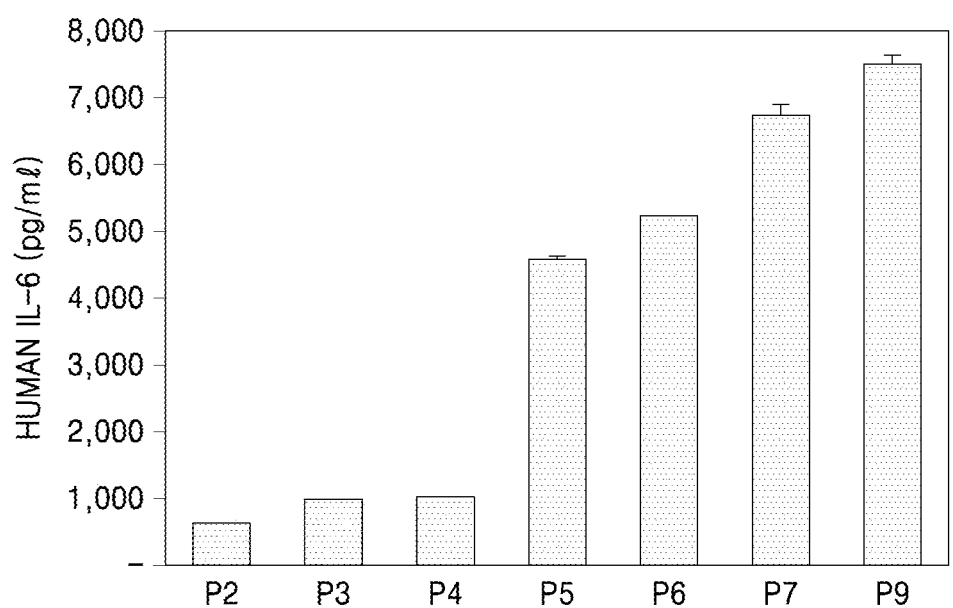
Figure 5E:
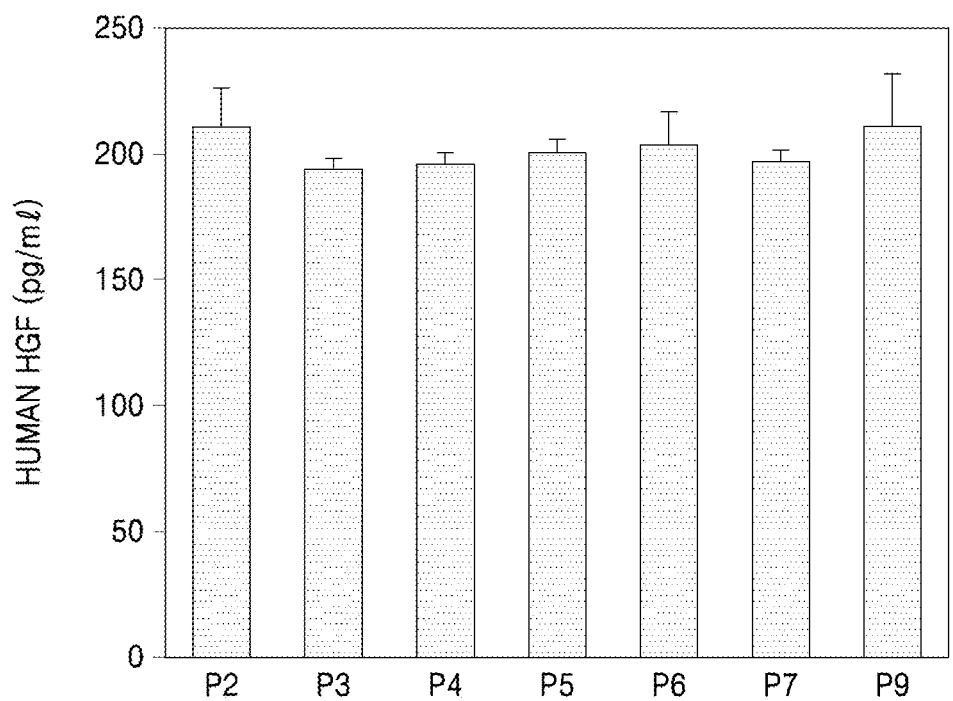

Results are shown in FIGS. 4A and 4B.

FIG. 4 shows morphological characteristics and genetic safety of adherent cells prepared by the method of preparing adherent cells according to a specific embodiment.

As shown in FIG. 4A, it was confirmed that the cells cultured to P14 maintained well their morphology, and had a morphology specific to fibroblasts with irregular protrusions and no genetic abnormality.

As shown in FIG. 4B, it was confirmed that the adherent cells cultured to P1, P3, and P6 had no chromosomal abnormalities.

Example 2: Profiling and Quantification Analysis of Secretory Proteins of Enhanced Postnatal Adherent Cells 1. Profiling of Secretory Proteins Profiling of secretory proteins was performed in order to analyze secretory proteins of the adherent cells prepared in 1 of Example 1.

In detail, the cultured adherent cells were allowed to secrete secretory proteins in serum-free MEM alpha GlutaMAX (Invitrogen), and secretory proteins were concentrated at a concentration of 1 mg/ml. The concentrate was used to analyze proteins secreted by the adherent cells by using a human antibody array (Raybio) capable of analyzing 504 kinds of secretory proteins.

As a result, as shown in the following Table 3, a total of 48 kinds of proteins were found to be secreted.

TABLE 3

| Rating | Cytokine |
| --- | --- |
| 1 | Thrombospondin (TSP) |
| 2 | EDA-A2 |
| 3 | IGFBP-rp1/IGFBP-7 |
| 4 | Thrombospondin-1 |
| 5 | MMP-1 |
| 6 | HGF |
| 7 | IL-8 |
| 8 | sgp130 |
| 9 | WIF-1 |
| 10 | IL-6 |
| 11 | TIMP-2 |
| 12 | GRO |
| 13 | Latent TGF-beta bp1 |
| 14 | GDF-15 |
| 15 | sFRP-4 |
| 16 | IL-19 |
| 17 | Kremen-2 |
| 18 | TGF-beta RIII |
| 19 | M-CSF |
| 20 | MSP alpha Chain |
| 21 | MIP 2 |
| 22 | TNF RI/TNFRSF1A |
| 23 | MCP-3 |
| 24 | Galectin-3 |
| 25 | MCP-1 |
| 26 | sFRP-1 |
| 27 | TGF-beta RI/ALK-5 |
| 28 | IL-15 R alpha |
| 29 | ENA-78 |
| 30 | IL-7 |
| 31 | SPARC |
| 32 | VEGF |
| 33 | Inhibin B |
| 34 | IGFBP-3 |
| 35 | Nidogen-1 |
| 36 | EMAP-II |
| 37 | Progranulin |
| 38 | MIF |
| 39 | IL-3 |
| 40 | IGFBP-6 |
| 41 | TIMP-1 |
| 42 | IGF-II R |
| 43 | Activin C |
| 44 | Smad 4 |
| 45 | Decorin |
| 46 | Dkk-1 |
| 47 | MIP-1a |
| 48 | FGF-7/KGF |

2. Quantification Analysis of Secretory Proteins

It was confirmed that some particular proteins of the secretory proteins were effective for neurological diseases, and VEGF, TGF-β1, progranulin, HGF, and IL-6 effective for regeneration of damage tissues were secreted. Quantification analysis thereof was performed.

The secreted amounts of the five proteins were analyzed by an enzyme-linked immunosorbant assay (ELISA). An equal number of cells at each passage was seeded in a 6-well plate, and cultured for 1 day. Then, serum-free MEM alpha GlutaMAX (Invitrogen) was replaced. After culturing for 1 day, this culture was used as a sample. Each of ELISA kits as in the following Table 4 was used and of them, TGF-β1 includes a pretreatment process of samples. All was measured at 450 nm by using a microplate reader Epoch (BioTek Inc.) and analyzed by using Gen5 (2.00) software. Results are shown in FIG. 5.

TABLE 4

| ELISA Kit | Product No. | Available source |
| --- | --- | --- |
| Human VEGF | DVE00 | R&D system |
| Human TGF-β1 | DB100B | R&D system |
| Human progranulin | DPGRN0 | R&D system |
| Human HGF | SEA047Hu | Uscn life Science Inc. |
| Human IL-6 | D6050 | R&D system |

FIG. 5 shows quantification result of proteins secreted by adherent cells according to subculturing of the adherent cells which were prepared by the method of preparing adherent cells according to a specific embodiment.

As shown in FIG. 5, it was confirmed that VEGF and IL-6 increased with passage, and 1,000 pg/ml or more of TGF-β1 and progranulin were secreted. These results suggest that adherent cells prepared according to a specific embodiment secrete neurological disease-specific proteins, thereby being usefully applied to cell therapeutic agents.

The invention claimed is:

1. A method of preparing enhanced postnatal adherent cells, the method comprising:
   obtaining an amniotic tissue from a detached placenta;
   harvesting cell populations by adding an enzyme mixed solution to the amniotic tissue, wherein the enzyme mixed solution comprises collagenase at a concentration of 0.5 mg/ml to 5 mg/ml, trypsin at a concentration of 1 mg/ml to 5 mg/ml, DNA hydrolase (DNase) at a concentration of 0.01 mg/ml to 0.05 mg/ml, and dispase at a concentration of 0.1 U/ml to 5 U/ml;
   isolating the enhanced postnatal adherent cells by culturing the harvested cell populations in a container by adhesion culture and then treating the cell populations with an animal component-free (ACF) recombinant enzyme; and
   subculturing the isolated enhanced postnatal adherent cells under a hypoxia condition lower than a normoxia condition of 21% in a medium containing fibroblast growth factor-4 (FGF-4) and heparin at least 6 passages, wherein the subculturing further comprises treatment of the animal component-free recombinant enzyme before transferring the cells for subculturing at every stage of subculturing, and
   wherein 80% or more of the adherent cells express CD44, CD73, CD90, and CD105-positive surface markers and 10% or less thereof express a CD45-negative surface marker, and more vascular endothelial growth factor (VEGF) and interleukin-6 (IL-6) are secreted compared to the isolated enhanced postnatal adherent cells of passages 1 to 4.

2. The method of claim 1, wherein the amniotic tissue from the amniotic tissue is obtained by scraping a chorionic plate membrane of the placenta to remove a chorion.

3. The method of claim 1, wherein the enzymatic reaction is performed at 30° C. to 40° C. for 5 minutes to 60 minutes under shaking.

4. The method of claim 1, wherein the hypoxic condition is at an oxygen partial pressure of 1% to 12%.

5. The method of claim 1, wherein the subculturing is performed from passage 6 to passage 20.

6. The method of claim 1, wherein the harvesting of the cell populations increases yield of adherent cells, as compared with no use of the enzyme mixed solution.

7. The method of claim 1, wherein a proliferation rate of the adherent cells is increased, as compared with that under a normoxia condition.

8. The method of claim 1, wherein the isolating of the adherent cells increases purity of the adherent cells, as compared with no use of the animal component-free recombinant enzyme.

9. The method of claim 1, wherein the prepared adherent cells secrete a protein selected from the group consisting of vascular endothelial growth factor (VEGF), transforming growth factor (TGF)-β1, hepatocyte growth factor (HGF), interleukin-6 (IL-6), progranulin, and combinations thereof.

10. A method of increasing a preparation efficiency of enhanced postnatal adherent cells, the method comprising:

harvesting cell populations by adding an enzyme mixed solution to an amniotic tissue, wherein the enzyme mixed solution comprises collagenase at a concentration of 0.5 mg/ml to 5 mg/ml, trypsin at a concentration of 1 mg/ml to 5 mg/ml, DNA hydrolase (DNase) at a concentration of 0.01 mg/ml to 0.05 mg/ml, and dispase at a concentration of 0.1 U/ml to 5 U/ml;

isolating enhanced postnatal adherent cells by culturing the harvested cell populations in a flask by adhesion culture and then treating the cell populations with an animal component-free (ACF) recombinant enzyme; and subculturing the isolated enhanced postnatal adherent cells under a hypoxia condition lower than a normoxia condition of 21% in a medium containing fibroblast growth factor-4 (FGF-4) and heparin at least 6 passages, wherein the subculturing further comprises treatment of the animal component-free recombinant enzyme before transferring the cells for subculturing at every stage of subculturing, and wherein 80% or more of the adherent cells express CD44, CD73, CD90, and CD105-positive surface markers and 10% or less thereof express a CD45-negative surface marker, and more vascular endothelial growth factor (VEGF) and interleukin-6 (IL-6) are secreted compared to the isolated enhanced postnatal adherent cells of passages 1 to 4.

11. The method of claim 10, wherein the increasing of the preparation efficiency of the adherent cells is increasing of yield of adherent cells, as compared with no use of the enzyme mixed solution, increasing of a proliferation rate of the adherent cells, as compared with that under a normoxia condition, or increasing of purity of the adherent cells, as compared with no use of the animal component-free recombinant enzyme.

* * * * *